United States Patent
Wei et al.

(10) Patent No.: US 6,372,246 B1
(45) Date of Patent: Apr. 16, 2002

(54) POLYETHYLENE GLYCOL COATING FOR ELECTROSTATIC DRY DEPOSITION OF PHARMACEUTICALS

(75) Inventors: Shifeng Bill Wei, Belle Mead; Herling Uang, Somerset, both of NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/212,886

(22) Filed: Dec. 16, 1998

(51) Int. Cl.$^7$ .............................. A61K 47/00; A61K 9/20

(52) U.S. Cl. ....................... 424/439; 424/464; 424/489; 427/2.14; 427/472

(58) Field of Search .................................. 424/439, 441, 424/489, 464; 106/244; 427/2.14, 472

(56) References Cited

U.S. PATENT DOCUMENTS

| | | | |
|---|---|---|---|
| 4,029,758 A | | 6/1977 | Mlodozeniec et al. |
| 4,031,200 A | * | 6/1977 | Reif |
| 4,197,289 A | | 4/1980 | Sturzenegger et al. |
| 4,302,440 A | | 11/1981 | John et al. |
| 4,940,665 A | * | 7/1990 | Iijima et al. |
| 5,224,989 A | | 7/1993 | Likarova |
| 5,470,603 A | | 11/1995 | Staniforth et al. |
| 5,669,973 A | | 9/1997 | Pletcher |
| 5,714,007 A | | 2/1998 | Pletcher et al. |

FOREIGN PATENT DOCUMENTS

| | | |
|---|---|---|
| WO | 9635413 | 11/1996 |
| WO | 9639257 | 12/1996 |
| WO | 9820861 | 5/1998 |

OTHER PUBLICATIONS

International Search Report Application No.PCT/US99/28377 dated Apr. 11, 2000.

Presentation at the American Assoc. of Pharmaceutical Scientists annual conference in San Francisco, CA on Nov. 15–19, 1998, Electrostatic Powder Coating of Tablets I: Design and Characteristics of a Continuous Coater Prototype.

Presentation at the American Assoc. of Pharmaceutical Scientists annual conference in San Francisco, CA on Nov. 15–19, 1998, Electrostatic Solid State Drug Loading Onto Tablet Substrate Surfaces.

Presentation at the American Assoc. of Pharmaceutical Scientists annual conference in San Francisco, CA on Nov. 15–19, 1998, Electrostatic Powder Coating of Tablets II: Electrostatic Characteristics of Coating Systems.

Presentation at the American Assoc. of Pharmaceutical Scientists annual conference in San Francisco, CA on Nov. 15–19, 1998, Electrostatic Powder Coating of Tablets III: Modification of Particle–Substrate Interactions.

Presentation at the American Assoc. of Pharmaceutical Scientists annual conference in San Francisco, CA on Nov. 15–19, 1998, Electrostatic Powder Coating of Tablets IV: Melt Rheology of Coating Powders.

* cited by examiner

*Primary Examiner*—Thurman K. Page
*Assistant Examiner*—Brian K. Seidleck
(74) *Attorney, Agent, or Firm*—Ellen Ciambrone Coletti

(57) ABSTRACT

The invention relates to a substrate coating for the electrostatic deposition of dry powder medicaments for use in the manufacture of pharmaceutical dosage forms comprising micronized polyethylene glycol (PEG), with A molecular weight in the range of 1,000 to 20,000, and having a particle size of 1–100 $\mu$m. The invention also relates to pharmaceutical compositions having such a substrate coating, and processes for manufacturing such pharmaceutical compositions. The invention also relates to the technology of reversing negative charge of medicaments so that they can be electrostatically deposited on a negatively charged substrate.

8 Claims, No Drawings

POLYETHYLENE GLYCOL COATING FOR ELECTROSTATIC DRY DEPOSITION OF PHARMACEUTICALS

FIELD OF THE INVENTION

The invention relates to substrate coatings for the electrostatic deposition of dry powder medicaments for use in the manufacture of pharmaceutical dosage forms. The invention also relates to the technology of reversing negative charge of medicaments so that they can be deposited on a negatively charged substrate. More particularly, the invention relates to polyethylene glycol substrate coatings for the dry powder electrostatic deposition of medicinal substances. The invention also provides the means of employing polyethylene glycol to reverse the negative charge of medicaments so that they can be deposited on a negatively charged substrate.

BACKGROUND OF THE INVENTION

It has been proposed for sometime that dry powdered medicaments be delivered orally by electrostatically depositing the dry medicament onto an edible substrate which could be administered to the patient. The substrate with the medicament deposited thereon is administered to the patient directly or is applied to a placebo tablet which can be administered to the patient. The technology has potential advantages in enhanced safety, enhanced stability, and efficient product development and manufacturing.

One example of this technique is disclosed in U.S. Pat. No. 4,197,289 (the '289 patent). This patent discloses solid unit dosage forms for oral administration comprising an edible "web" having the medicament deposited thereon where the web is fabricated into a dosage form in which the deposited medicament is sealed. The dosage forms are manufactured by using an electrostatic charging technique. In this technique, the edible web is passed through an electrostatic field in a suitable chamber. Finely particulate active ingredient is introduced into the chamber and is deposited onto the web as it passes over an oppositely charged roller. Dosages are regulated by measuring spectroscopically the amount of medicament that has been deposited on the web and fabricating an appropriate dosage form with the required amount of medicament. In this technique, the edible web used for depositing the medicament is an edible material with a resistivity capable of enabling the deposition thereon of dielectric particles. Paper and polymeric web formulations are disclosed. The polymeric webs are prepared from an organic film forming polymer such as cellulose derivatives in combination with plasticizers, modifiers and fugitive solvents.

Another technique is disclosed in U.S. Pat. No. 5,714,007 (the '007 patent). In this patent there is disclosed an apparatus and method for electrostatically depositing select doses of medicament powder at select locations on a substrate. The '007 patent technique involves charging a predefined region of a substrate with a controlled amount of charge. Oppositely charged medicament powder is then exposed to the charged substrate so that the powder medicament adheres to the charged substrate. The quantity and position of charge accumulated on the substrate and the charge-to-mass ratio of the medicament powder can be used to accurately control the dosage of medicament applied to the substrate and the position of the medicament on the substrate. The substrate is then encapsulated in an inert material to form a capsule, tablet, or suppository. It is suggested that the substrates can vary widely depending upon the ultimate application of the medication. For oral medications, polymeric substances such as cellulose are disclosed.

In each of these techniques it is suggested that the dry powder can be applied directly to the surface of the edible substrate and the substrate can either be divided into unit dosage forms or encapsulated in an inert material to form a capsule, tablet or suppository. In either case, when the dry medicament powder is deposited directly onto a dosage form substrate, a coating is required. The deposited drug powder is as loose as dust on the surface of a furniture. To prevent drug powder from being wiped off or from losing potency during subsequent processing and packaging, the product needs a protective coating.

Various materials are used as film coatings in tablet manufacture but in practice conventional polymeric coatings are not all suitable. Polymeric films typically used in such film coating include (1) vinyl polymers such as polyvinylpyrrolidone, polyvinyl alcohol and acetate, (2) cellulosics such as methyl and ethyl cellulose, hydroxyethyl cellulose and hydroxypropyl methylcellulose, (3) acrylates and methacrylates, (4) copolymers such as the vinyl-maleic acid and styrene-maleic acid types, and (4) natural gums and resins such as zein, gelatin, shellac and acacia. See Remington's Pharmaceutical Sciences, 15th Ed. Mack Publishers (1975) p. 1613.

For the present purposes, the coating needs to be applied to the individual dosage forms precisely and in place. The conventional coating of tablets is random coating. The process includes spraying the coating solution onto a tablet bed while the tablet bed is tumbling in a coating pan. A coating film is formed on the tablets when water or solvent is dried at elevated temperature during coating. The conventional coating is suitable for conventional pharmaceutical dosage forms, tablets or capsules, since the drug substance is embedded or encapsulated in the tablet matrix or capsules. But the conventional coating is not suitable for deposited tablets produced by Electrostatic Dry Deposition technology due to the tumbling of the tablet bed. The coating should be in-place: the deposited tablet or product needs to be coated before it comes in contact with other tablets. In the mean time, the coating should be precise: all coating solution should be on the tablet. Any spill may cause insulation of or interference with the electronic equipment. Accordingly, there is a need for a protective substrate coating which is suitable for the electrostatic deposition of dry powder medicaments which can be applied in place and precisely.

Another problem that is encountered in the above described electrostatic deposition method is that the triboelectric charging process generally produces positively charged drug substances and negatively charged substrate. However, some drug substances can only be negatively charged and would not be suitable for use with a negatively charged substrate. Accordingly, a need exists for a method of depositing negatively charged drug substance on a negatively charged substrate.

SUMMARY OF THE INVENTION

The invention relates to a substrate coating for the electrostatic deposition of dry powder medicaments for use in the manufacture of pharmaceutical dosage forms comprising micronized polyethylene glycol (PEG), with molecular weight in the range of 1,000 to 20,000, and having a particle size of 1–100 μm.

The invention also relates to an improvement in the process for manufacturing pharmaceutical unit dosage forms by triboelectric charging and the electrostatic deposition of dry powder medicament to a substrate, the improvement comprising coating the substrate in place with dry micronized polyethylene glycol (PEG), melting the dry polyethylene glycol coating and allowing it to cool whereupon a protective coating is formed.

In a further aspect of the invention, a method of depositing negatively charged dry powder medicament on a negatively charged substrate by an electrostatic dry powder deposition process is provided, the method comprising reversing the charge of the medicament to a positive charge by mixing the negatively charged medicament with micronized polyethylene glycol (PEG), at the ratio of medicament to PEG of 1:1 to 1:40, and then depositing the mixture onto the negatively charged substrate. Once the charged mixture is deposited on the substrate surface, it is melted and cooled whereupon a protective film is formed while cooling.

In a further aspect of the invention, a pharmaceutical composition is provided comprising an edible substrate having micronized drug substance with a particle size of 1–100 µm, preferably 5–20 µm, deposited on the surface of the substrate by electrostatic dry powder deposition, and a film coating on the substrate and drug substance consisting essentially of micronized polyethylene glycol (PEG), with molecular weight in the range of 1,000 to 20,000, and having a particle size of 1–100 µm. In a preferred embodiment, the edible substrate is comprised of a tablet core. Preferably, the drug substance is selected from one or more estrogen and/or progestins, preferably norgestimate and ethinyl estradiol.

DETAILED DESCRIPTION

The use of micronized PEG as a protective coating in accordance with the present invention provides several unique advantages. PEG has a low contact angle. Therefore, it can penetrate through the deposited powder and make contact with the substrate surface. As a result, PEG can form a strong coating even in the presence of loose powder between coating film and substrate. Further, PEG has a desirable melting range: 50–63° C., depending on the molecular weight. This melting point is prodigiously suited for the present purposes since melting points lower than 40–50° C. may cause sticking and flow problems during processing and packaging, while melting points higher than 65–70° C. may cause slow dissolution, and low bioavailability of drug products. Moreover, PEG is water soluble. Its coating will not delay the dissolution of drug products. Therefore, PEG will not affect bioavailability of drug products.

Furthermore, the PEG coating of the present invention can be applied to the substrate precisely and in-place to avoid spillage and interference with the electronic deposition equipment. PEG is deposited in place by completion of the deposition process while substrates are still on the tray, platform, or conveyer belt. The in-place coating can avoid detachment of the medicaments in a tablet bed as encountered in the conventional tumbling-dry coating process. Moreover, the protective coating formed by the micronized PEG of the present invention provides a pharmaceutically elegant cosmetic coating into which colorants and other additives can be incorporated to improve the appearance, feel and dissolution characteristics.

In another aspect of the invention, as stated above, the coating process of the present invention can be employed to reverse the charge of negatively charged drug substance for deposition on a negatively charged substrate. Triboelectric charging can only produce one particular charge, positive or negative charge, for a particular substance or medicament. By employing the micronized PEG at the described mixing ratio, the negatively charged drug substance can be converted to a positively charged powder for deposition. The uniqueness of the process lies in the PEG molecule which contains abundant oxygen atoms. The oxygen atoms are electronegative, i.e., they pull electrons to them. The surplus electrons demonstrate as a negative charge of drug substance. Once PEG mixes with drug substance, the oxygen atoms in PEG molecule will "neutralize" the surplus electrons of drug substance. As a result, the mixture of PEG and drug substance demonstrate a net positive charge. Therefore, the mixture can be deposited to the negatively charged substrate.

In accordance with the present invention, the PEG coating is formed on at least a portion, preferably on all, of the exposed surface of the substrate containing the pharmaceutical actives. The substrate may be an edible polymer film or may be a pharmaceutical tablet core or placebo tablet. Suitable polymer films which may be used as edible substrates are selected from art recognized non-toxic organic film formers such as natural and chemically modified starches and dextrins, proteins such as gelatins; cellulose derivatives such as sodium carboxymethylcellulose, hydroxypropylmethylcellulose and the like; other polysaccharides such as pectin, xanthan gum, guar gum, algin and the like; and synthetic film forming polymers such as polyvinylpyrrolidone. Suitable polymer substrates are disclosed in U.S. Pat. No. 4,029,758, hereby incorporated by reference. Suitable tablet cores or placebo tablets which may be used as substrates are selected from art recognized tableting ingredients. The cores are prepared in accordance with standard pharmaceutical tableting techniques, including wet-granulation, dry-granulation, direct compression, spheronization and the like. Preferably the tablet cores are prepared by compressing a mixture of microcrystalline cellulose (99–99.5%) and magnesium stearate (0.5–1%).

The PEG film coating may optionally contain a plasticizer, such as castor oil, polyethylene glycol, propylene glycol or glycerine, but in most cases a plasticizer will not be required. The coating may also contain a coloring or pacifying agent. The film coating may also contain a flavoring and/or sweetening agent to improve palatability.

The preferred PEG coating material will generally be composed of micronized PEG having a molecular weight in the range of 1,000 to 20,000 and a particle size of 1–100 µm, with a melting point in the range of 50–63° C. Preferably PEG 6000–8000, is employed. The PEG material is micronized by way of air attrition, e.g., by use of a Jetmill, to a particle size of 1–100 µm, preferably 5–10 µm. Obviously equivalents for these compounds as are well known in the tablet coating art, may be used in approximately the same proportions.

The protective coating is applied to the substrate as a dry powder by electrostatic dry deposition using the techniques known in the art such as those disclosed in U.S. Pat. Nos. 4,029,758, 5,714,007, 5,788,814 and 5,470,603, hereby incorporated by reference. Once the dry coating powder is deposited on the surface of the substrate, it is melted and cooled to form a thin film coating.

The PEG film coating (dried) generally constitutes from about 1 to about 10, preferably about 2 to about 6, percent by weight of the total weight of the solid dosage form.

The PEG film coatings of the present invention may be employed for the coating of a variety of medicaments where electrostatic deposition manufacturing techniques are desirable. Typically, the active ingredient will be a dry powder medicament in which small (i.e. microgram) dosages are needed and where exposure to the active ingredient during manufacture must be kept to a minimum, for example hormones or cytotoxic medicaments. These medicaments are most suited for electrostatic dry deposition processes. The preferred pharmaceutical tablets with which the PEG protective coatings of the present invention is used contains an estrogen optionally in combination with a progestin for use as oral contraceptives. Preferably, the estrogen component is employed in a daily dosage equivalent to about 0.020–0.050 mg of ethinyl estradiol, preferably about 0.030 mg ethinyl estradiol equivalent. The progestin component is preferably administered in a daily dosage corresponding in progestational activity to 0.065–2.0 mg norethindrone per day. Norgestimate in an amount of about 30–250 $\mu$g with or without 35 $\mu$g of ethinyl estradiol is preferred. Other active ingredients which may be employed include cytotoxic agents, estradiol, estradiol cypionate, estradiol valerate, esterified estrogens, estrone, estropipate, quinestrol, mestranol, levonorgestrel, norethindrone, norgestrel and progesterone Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLE 1.

Norgestimate Tablet

PEG with molecular weight in the range of 1,000 to 20,000, preferably PEG 6000–8000, is micronized by way of air attrition, e.g., Jetmill, to a particle size of 1–100 $\mu$m preferably 5–10 $\mu$m. Norgestimate is micronized separately to particle size of 1–100 $\mu$m, preferably 5–20 $\mu$m. A placebo tablet is made by compressing the mixture of microcrystalline cellulose (99–99.5%) and magnesium stearate (0.5–1%). Placebo tablets are arranged in a tray of 9 tablets by 9 tablets array for deposit. Micronized norgestimate powder is triboelectrically charged. The amount of norgestimate to be deposited is based on the norgestimate charge/mass ratio. Adjust the charge of the substrate so that 250 $\mu$g of norgestimate is deposited on the substrate (placebo tablet) surface. Micronized PEG 8000 is triboelectrically charged, and deposited on top of norgestimate. Adjust the charge to deposit PEG in the range of 0.1–1.5 mg. Surface deposited PEG is placed under Infrared lamp until elted. PEG will form a coating film while cooling. In the similar manner, deposit PEG and coat bottom side and rest of the tablet surface.

EXAMPLE 2.

Norgestimate Tablet with Marketing Image

In most cases, substrate needs to incorporate colorant to give the dosage form a traditional appearance. PEG with molecular weight in the range of 1,000 to 20,000, preferably PEG 6000–8000, is micronized by Jetmill together with a colorant, e.g., iron oxide, to particle size of 5–10 μm. Micronized norgestimate powder is triboelectrically charged, and deposited on the substrate surface. Micronized PEG 6000/iron oxide mixture is triboelectrically charged, and deposited on top of norgestimate. Surface deposited PEG is placed under Infrared lamp until melt. PEG will form a coating film while cooling. In the similar manner, deposit PEG/iron oxide mixture and coat bottom side and rest of the tablet surface.

Tablet with marketing image can also be produced by coating micronized PEG on colored placebo tablets. Colored placebo tablet can be made by compressing the microcrystalline cellulose (99%), magnesium stearate (0.5%), iron oxide (0.05%).

EXAMPLE 3.

Norgestimate/Ethinyl Estradiol Tablet

PEG with molecular weight in the range of 1,000 to 20,000, preferably PEG 6000–8000, is micronized by Jet mill together with ethinyl estradiol at the ratio of ethinyl estradiol to PEG 1:1 to 1:60, , preferably 1:30 to 1:42. Adjust Jet mill to produce particle size of 1–100 μm, preferably 5–10 μm. Micronized norgestimate powder is electrically charged, and deposited on the substrate surface. Micronized PEG 6000/ethinyl estradiol mixture is electrically charged, and deposited on top of norgestimate. Surface deposited PEG is place under Infrared lamp until melt. PEG will form a coating film while cooling. In the similar manner, deposit PEG ethinyl estradiol mixture and coat bottom side and rest of the tablet surface. Adjust the charge of the substrate so that total of 250 μg of norgestimate and 35 μg of ethinyl estradiol are deposited on the substrate (placebo tablet) surface.

EXAMPLE 4.

Norgestimate Tablet with Marketing Image

Placebo tablets are arranged in a tray of 9 tablets by 9 tablets array for deposit. PEG 6000, is micronized by Jetmill together with iron oxide to particle size of 5–10 μm. Norgestimate is micronized separately to particle size of 5–15 μm. Micronized norgestimate powder is triboelectrically charged, and deposited on the substrate surface. Micronized PEG 6000/iron oxide mixture is triboelectrically charged, and deposited on top of norgestimate. Surface deposited PEG is place under infrared lamp until melt. Turn off the infrared lamp. PEG will form a coating film while cooling. In the similar manner, deposit PEG/iron oxide mixture and coat bottom side and rest of the tablet surface.

EXAMPLE 5.

Norgestimate/Ethinyl Estradiol Tablet

PEG 8000 is micronized by Jet mill together with ethinyl estradiol at the ratio of ethinyl estradiol to PEG from 1:1 to 1:60. Adjust Jet mill to produce particle size of 5–10 μm. Norgestimate is micronized separately to particle size of 5–15 μm. Micronized norgestimate powder is electrically charged, and deposited on the substrate surface. Micronized PEG 8000/ethinyl estradiol mixture is triboelectrically charged, and deposited on top of norgestimate.

Surface coating is accomplished by melting deposited PEG and cooling to form the coating. In the similar manner, deposit PEG only or PEG ethinyl estradiol mixture and coat bottom side and rest of the tablet surface. Adjust the charge of the substrate so that total of 250 μg of norgestimate and 35 μg of ethinyl estradiol are deposited on the substrate (placebo tablet) surface.

What is claimed is:

1. A pharmaceutical composition comprising an edible substrate having micronized drug substance with a particle size of 1–100 µm deposited on the surface of the substrate by electrostatic dry powder deposition, and a film coating on the substrate and drug substance consisting essentially of polyethylene glycol, wherein the film coating is applied by:

(a) coating the substrate in place by electrostatic dry powder deposition with dry micronized polyethylene glycol having a molecular weight in the range of 1,000 to 20,000 and having a particle size of 1–100 µm, and (b) melting the dry polyethylene glycol coating and allowing it to cool whereupon a protective coating is formed.

2. The pharmaceutical composition of claim 1 wherein the film coating has a melting point in the range of 50–63° C.

3. The pharmaceutical composition of claim 1 wherein the PEG has a molecular weight in the range of 6,000–8,000.

4. The pharmaceutical composition of claim 1 wherein the PEG film coating (dried) constitutes from about 1 to about 10, percent by weight of the total weight of the solid dosage form.

5. The pharmaceutical composition of claim 1 wherein the edible substrate is comprised of a tablet core.

6. The pharmaceutical composition of claim 2 wherein the tablet core is prepared by compressing a mixture of microcrystalline cellulose (99–99.5%) and magnesium stearate (0.5–1%).

7. The pharmaceutical composition of claim 1 wherein the drug substance is selected from one or more estrogens and/or progestins.

8. The pharmaceutical composition of claim 7 wherein the drug substance is a combination of norgestimate and ethinyl estradiol.

* * * * *